(12) United States Patent
Ariyama et al.

(10) Patent No.: US 11,000,219 B2
(45) Date of Patent: May 11, 2021

(54) ELECTROCARDIOGRAM MEASUREMENT APPARATUS AND ELECTROCARDIOGRAM MEASUREMENT METHOD

(71) Applicant: NEC Corporation, Tokyo (JP)

(72) Inventors: Tetsuri Ariyama, Tokyo (JP); Masahiro Kubo, Tokyo (JP); Katsumi Abe, Tokyo (JP); Ersin Altintas, Tokyo (JP); Yuji Ohno, Tokyo (JP); Takeshi Akagawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 322 days.

(21) Appl. No.: 15/767,167

(22) PCT Filed: Sep. 20, 2016

(86) PCT No.: PCT/JP2016/004270
§ 371 (c)(1),
(2) Date: Apr. 10, 2018

(87) PCT Pub. No.: WO2017/068751
PCT Pub. Date: Apr. 27, 2017

(65) Prior Publication Data
US 2018/0289273 A1    Oct. 11, 2018

(30) Foreign Application Priority Data

Oct. 21, 2015  (JP) .............................. JP2015-207322

(51) Int. Cl.
*A61B 5/0408*  (2006.01)
*A61B 5/0428*  (2006.01)
(Continued)

(52) U.S. Cl.
CPC ............... *A61B 5/25* (2021.01); *A61B 5/282* (2021.01); *A61B 5/291* (2021.01); *A61B 5/296* (2021.01);
(Continued)

(58) Field of Classification Search
CPC . A61B 5/0408; A61B 5/0402; A61B 5/04085; A61B 5/0428; A61B 5/0478; A61B 5/0492; A61B 5/489; A61B 5/7203
See application file for complete search history.

(56) References Cited

U.S. PATENT DOCUMENTS 4,360,030 A * 11/1982 Citron .................. A61B 5/0432
                                                          600/515
4,692,148 A     9/1987 Kantrowitz et al.
(Continued)

FOREIGN PATENT DOCUMENTS

JP       51-032082 A     3/1976
JP       S62-236532 A   10/1987
(Continued)

OTHER PUBLICATIONS

International Search Report for PCT Application No. PCT/JP2016/004270, dated Dec. 13, 2016.
(Continued)

*Primary Examiner* — Lindsey G Wehrheim

(57) ABSTRACT

An object of the present invention is to provide an electrocardiogram measurement apparatus capable of significantly reducing the number of electrodes and measuring even a faint signal. The present invention provides an electrocardiogram measurement apparatus including a first electrode and a second electrode to be brought into contact with a body surface near an artery, an electrocardiogram measurement means for measuring a signal obtained from the first electrode and the second electrode, an artery position measurement means for identifying a position at which a measured value of a measured signal is largest as a position of an artery; and a notification means for notifying a user of information indicating the position of an artery.

15 Claims, 15 Drawing Sheets

(51) Int. Cl.
*A61B 5/0478* (2006.01)
*A61B 5/0492* (2006.01)
*A61B 5/0402* (2006.01)
*A61B 5/00* (2006.01)
*A61B 5/25* (2021.01)
*A61B 5/30* (2021.01)
*A61B 5/282* (2021.01)
*A61B 5/291* (2021.01)
*A61B 5/296* (2021.01)
*A61B 5/318* (2021.01)

(52) U.S. Cl.
CPC ............... *A61B 5/30* (2021.01); *A61B 5/318* (2021.01); *A61B 5/489* (2013.01); *A61B 5/7203* (2013.01)

(56) References Cited

U.S. PATENT DOCUMENTS

| | | | |
|---|---|---|---|
| 6,334,850 | B1 | 1/2002 | Amano et al. |
| 8,961,420 | B2* | 2/2015 | Zhang ................. A61B 8/0891 600/407 |
| 2004/0082850 | A1* | 4/2004 | Bonner .................... A61B 5/06 600/424 |
| 2006/0264770 | A1 | 11/2006 | Wellens et al. |
| 2010/0076328 | A1 | 3/2010 | Matsumura et al. |

FOREIGN PATENT DOCUMENTS

| | | |
|---|---|---|
| JP | H08-71048 A | 3/1996 |
| JP | 2004-242851 A | 9/2004 |
| JP | 2005-131356 A | 5/2005 |
| JP | 2005-151356 A | 5/2005 |
| JP | 2007-510493 A | 4/2007 |
| JP | 2008-136655 A | 6/2008 |
| JP | 5428889 B2 | 2/2014 |
| WO | 99/25242 A1 | 5/1999 |

OTHER PUBLICATIONS

English translation of Written opinion for PCT Application No. PCT/JP2016/004270.
Japanese Office Action for JP Application No. 2017-546393 dated Sep. 8, 2020 with English Translation.

* cited by examiner

ELECTROCARDIOGRAM MEASUREMENT APPARATUS AND ELECTROCARDIOGRAM MEASUREMENT METHOD

This application is a National Stage Entry of PCT/JP2016/004270 filed on Sep. 20, 2016, which claims priority from Japanese Patent Application 2015-207322 filed on Oct. 21, 2015, the contents of all of which are incorporated herein by reference, in their entirety.

TECHNICAL FIELD

The present invention relates to an electrocardiogram measurement apparatus and an electrocardiogram measurement method.

BACKGROUND ART

When an electrocardiogram is measured, typically many electrodes need to be attached to a plurality of body regions such as limbs and a chest. As a technique for measuring an electrocardiogram from a certain body region, an electrocardiogram measurement technique is described in PTL 1 that performs electrocardiogram measurement on an upper arm. In the technique described in PTL 1, eight or more electrodes are attached to an upper arm and the largest electrocardiographic signal is obtained from the electrodes.

PTL 2 discloses a pulse wave measuring electrode unit. The pulse wave measuring electrode unit is equipped with a pair of current applying electrodes and a pair of voltage measuring electrodes provided between and in line with the current applying electrodes, and measures a pulse wave while the electrode unit is in contact with a surface of a living body. PTL 2 claims that a pulse wave can be measured on a wrist with a high degree of accuracy since a percentage of current that flows through biotissue outside an artery is smaller.

CITATION LIST

Patent Literature

[PTL 1] Japanese Patent Publication No. 5428889
[PTL 2] Japanese Unexamined Patent Application Publication No. 2008-136655
[PTL 3] Japanese Unexamined Patent Application Publication No. H08-071048

SUMMARY OF THE INVENTION

Technical Problem

The technique described in PTL 1 requires many electrodes and therefore inconvenience to a user is not reduced as compared with common electrocardiogram measurement apparatuses. In addition, the technique does not provide a fundamental solution to an issue that signal processing time required for finding an electrocardiographic signal having the largest amplitude increases as the number of electrodes increases.

PTL 2 is not for electrocardiogram but for pulse waves and requires four electrodes.

Object of Invention

An object of the present invention is to provide an electrocardiogram measurement apparatus and an electrocardiogram measurement method that are capable of significantly reducing the number of electrodes and measuring even a faint signal, thereby resolving the technical issue described above.

Solution to Problem

The present invention provides an electrocardiogram measurement apparatus including: a first electrode and a second electrode to be brought into contact with a body surface near an artery; an electrocardiogram measurement means for measuring a signal obtained from the first electrode and the second electrode; an artery position measurement means for identifying an area in which polarity of a measured signal is reversed as a position of an artery; and a notification means for notifying a user of information indicating the position of an artery.

The present invention also provides an electrocardiogram measurement apparatus including: a first electrode and a second electrode to be brought into contact with a body surface near an artery; an electrocardiogram measurement means for measuring a signal obtained from the first electrode and the second electrode; an artery position measurement means for identifying a position at which a measured value of a measured signal is largest as a position of an artery; and a notification means for notifying a user of information indicating the position of an artery.

The present invention also provides an electrocardiogram measurement method including: measuring a signal obtained from a first electrode and a second electrode while moving the first electrode and the second electrode in contact with a body surface; and measuring an electrocardiogram by identifying an area in which polarity of a measured signal is reversed as a position of an artery.

Advantageous Effects of the Invention

According to the present invention, there are provided an electrocardiogram measurement apparatus and an electrocardiogram measurement method that use a significantly less number of electrodes and are capable of measuring even a faint signal.

DESCRIPTION OF EMBODIMENTS

Example embodiments of the present invention will be described below in detail with reference to the drawings. Note that the present invention is not limited to the example embodiments described below.

First Example Embodiment

Figure 1:
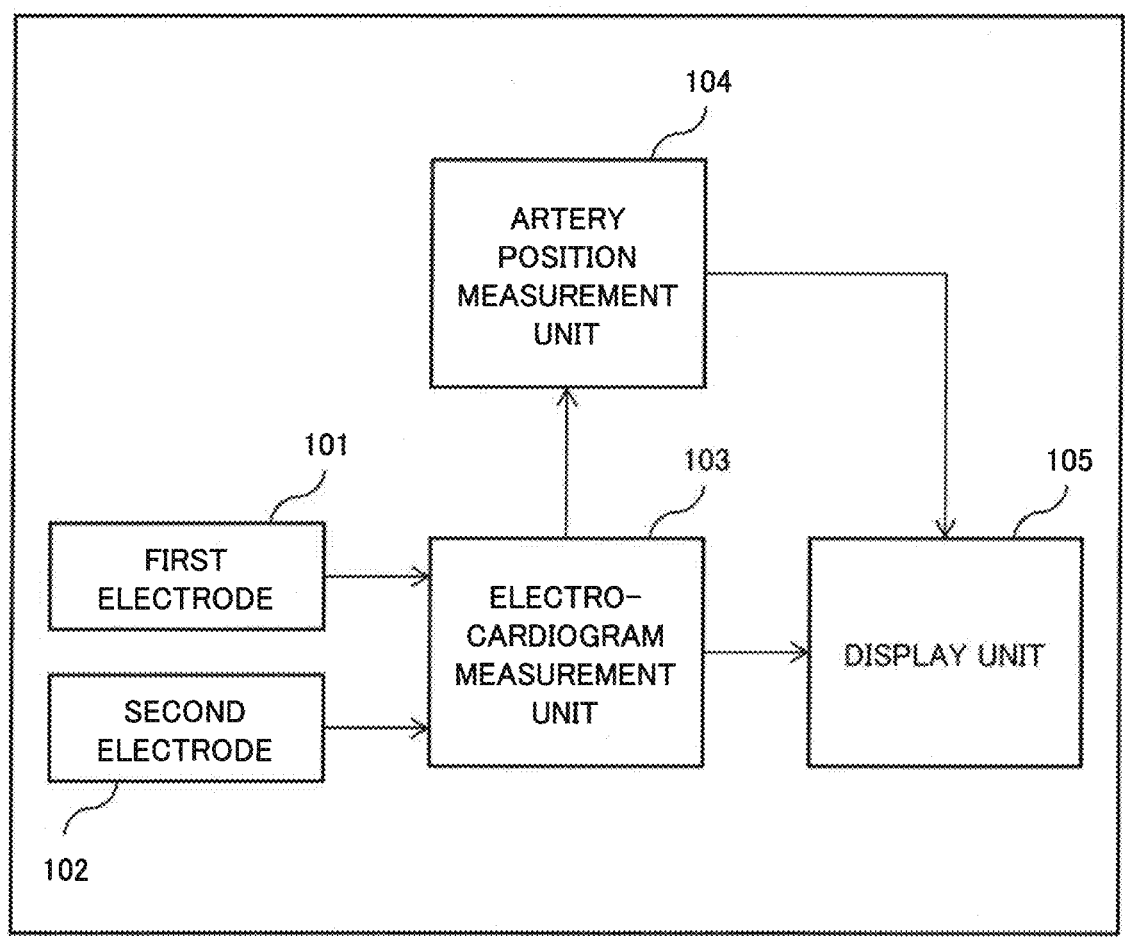
FIG. 1 is a block diagram of an electrocardiogram measurement apparatus of a first example embodiment according to the present invention.
Figure 2:
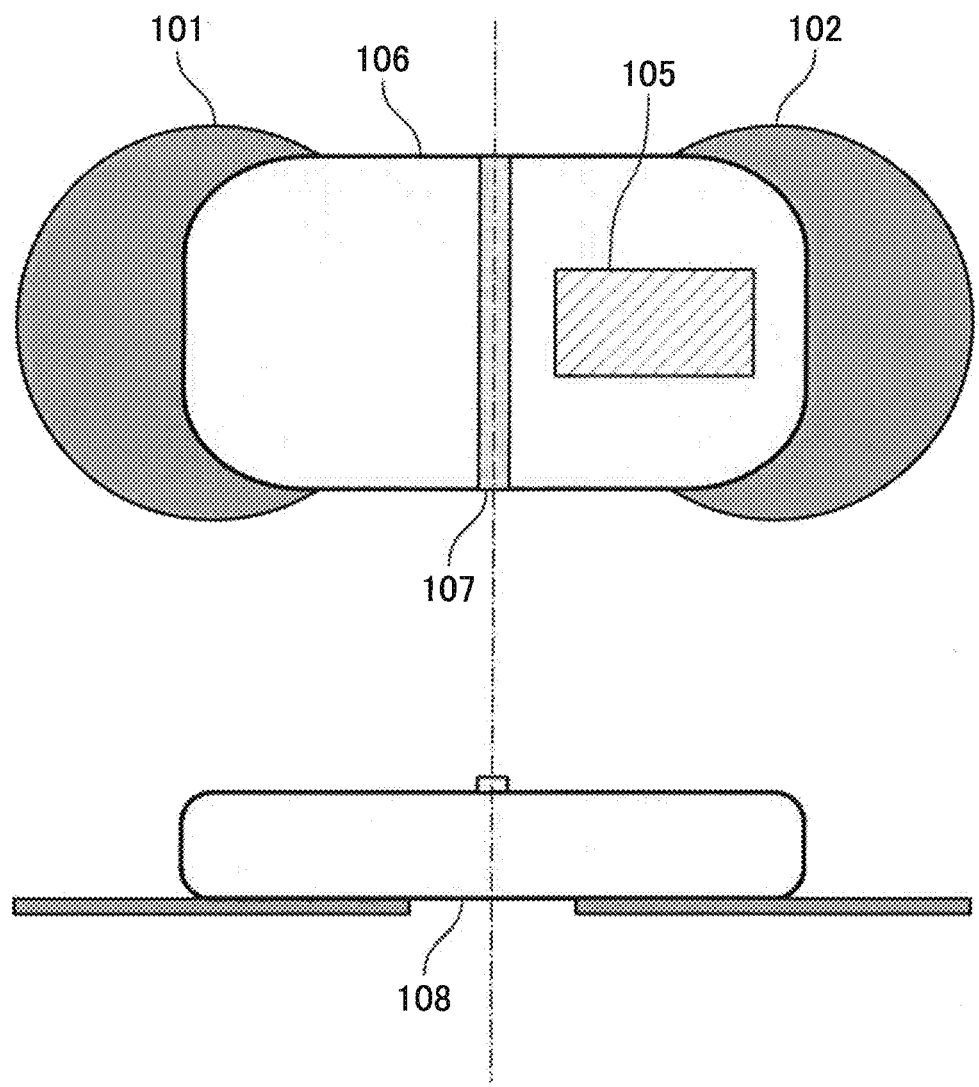
FIG. 2 illustrates a plan view and a cross-sectional view of the electrocardiogram measurement apparatus of the first example embodiment according to the present invention.

FIG. 1 is a block diagram of an electrocardiogram measurement apparatus of a first example embodiment of the present invention. The electrocardiogram measurement apparatus 100 includes a first electrode 101, a second electrode 102, an electrocardiogram measurement unit 103, an artery position measurement unit 104, and a display unit 105. FIG. 2 illustrates a plan view and a cross-sectional view of the electrocardiogram measurement apparatus 100. The first electrode 101 and the second electrode 102 are electrodes that obtain an electrocardiogram representing faint electrical signals flowing through a whole body. The first electrode 101 and the second electrode 102 are provided at ends of a housing 106. The first electrode 101 and the second electrode 102 each have an adhesive surface that makes contact with a body surface and allow the electrocardiogram measurement apparatus 100 to be attached to any position. Note that the first electrode 101 and the second electrode 102 in the present example embodiment have a circular planar shape.

Figure 3:
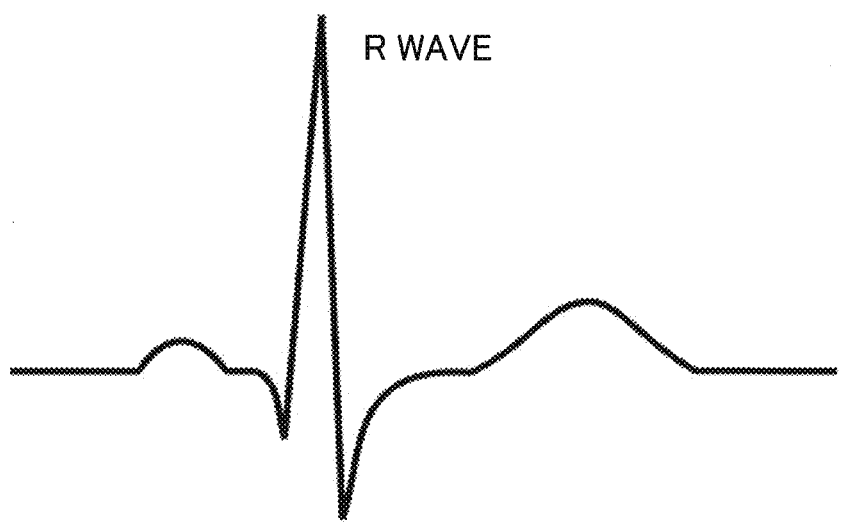
FIG. 3 illustrates a basic waveform of an electrocardiogram.

The electrocardiogram measurement unit 103 calculates a potential difference between the first electrode 101 and the second electrode 102 in contact with a body surface to obtain an electrocardiogram as illustrated in FIG. 3. Heart rate also can be measured by calculating the distance between peaks of R wave from the obtained electrocardiogram. The artery position measurement unit 104 calculates the largest value of an electrocardiographic signal obtained by the electrocardiogram measurement unit 103 and estimates the position of an artery. The display unit 105 displays results of calculations by the electrocardiogram measurement unit 103 and the artery position measurement unit 104. A display method is to display a waveform of an electrocardiogram and a heart rate, for example, as results of measurement by the electrocardiogram measurement unit 103. The display may be in any form that can be recognized by a user, and results of measurement by the artery position measurement unit 104 may be displayed as values themselves or may be displayed by changing the brightness or blinking rate of a light emission diode (LED) depending on the magnitude of the values. In addition, text may be displayed to indicate that a measurement position has been reached or is approaching.

Figure 4:
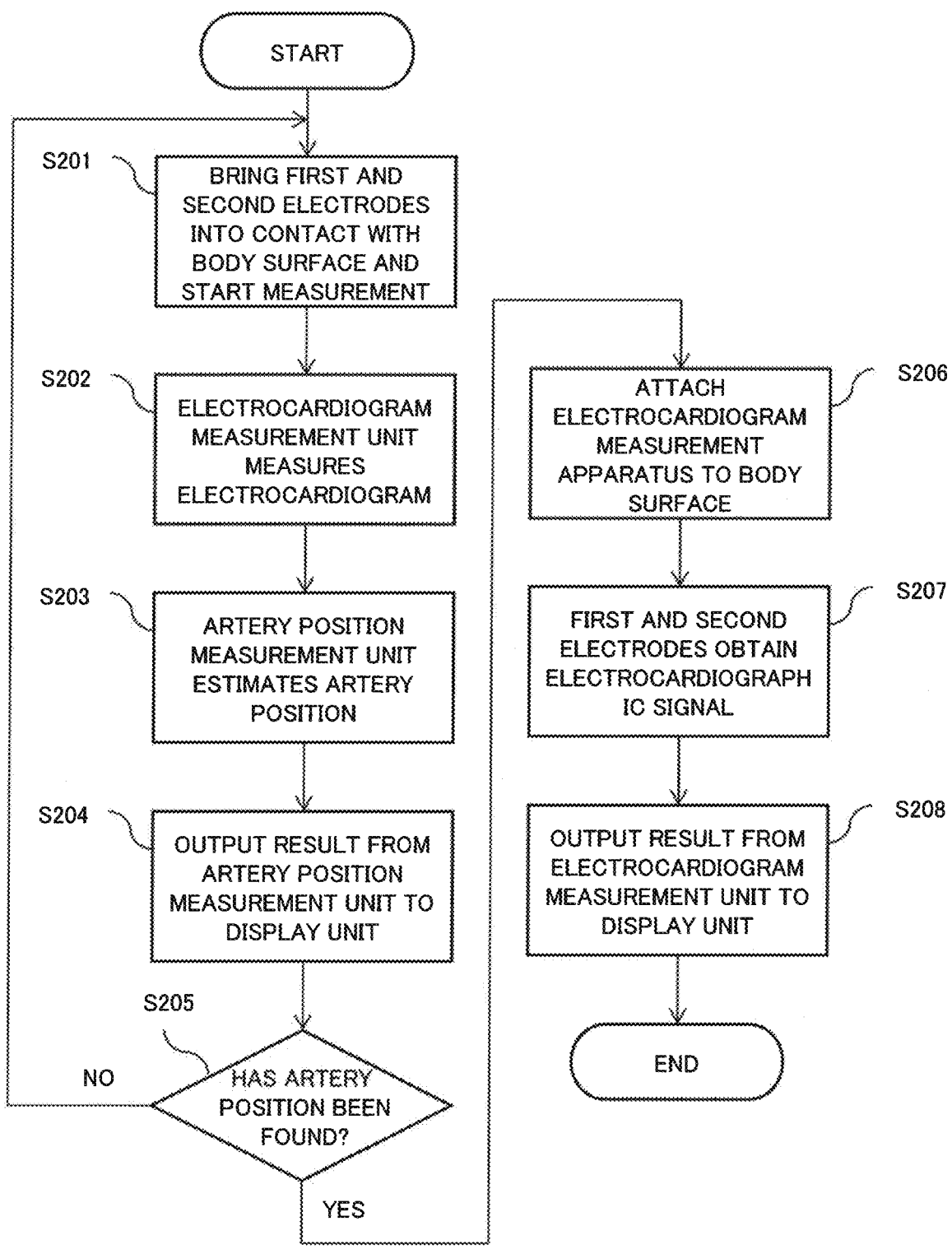
FIG. 4 is a flowchart of an operation procedure in the first example embodiment according to the present invention.

FIG. 4 is a flowchart illustrating a procedure of use of the electrocardiogram measurement apparatus 100. A user first brings the first electrode 101 and the second electrode 102 of the electrocardiogram measurement apparatus 100 into contact with a body surface near an artery in order to locate an artery (S201). It is preferable that the direction linking the first electrode 101 and the second electrode 102 is at right angles to the direction in which the artery extends. The electrocardiogram measurement apparatus 100 can measure an electrocardiogram when an artery is located between the first electrode 101 and the second electrode 102 (S202). The artery position measurement unit 104 estimates an artery position depending on a value from the electrocardiogram measurement unit 103 (S203) and outputs a result of the estimation to the display unit 105 (S204).

The user searches for optimum positions of the first electrode 101 and the second electrode 102 while observing output results on the display unit 105 (S205). Optimum positions are positions in which the potential difference between the first electrode 101 and the second electrode 102 is largest compared with those in other positions. This is repeated until optimum electrode positions are found (S205→S201). Since measurement is performed over a brachial artery 2 of the left upper arm 1 in the present example embodiment, the user moves the housing 106 in an arm circumferential direction in such a way that the potential difference increases.

Once an appropriate electrode is found, the electrocardiogram measurement apparatus 100 is fixed on the body surface (S206). The position is a position in which an artery position indication mark 107 overlaps the artery. The artery position indication mark 107 is in the center between the first electrode 101 and the second electrode 102 and is a linear raised portion of a surface of the housing 106. The artery position indication mark 107 serves as a positioning marker when the electrocardiogram measurement apparatus 100 is fixed.

Figure 5:
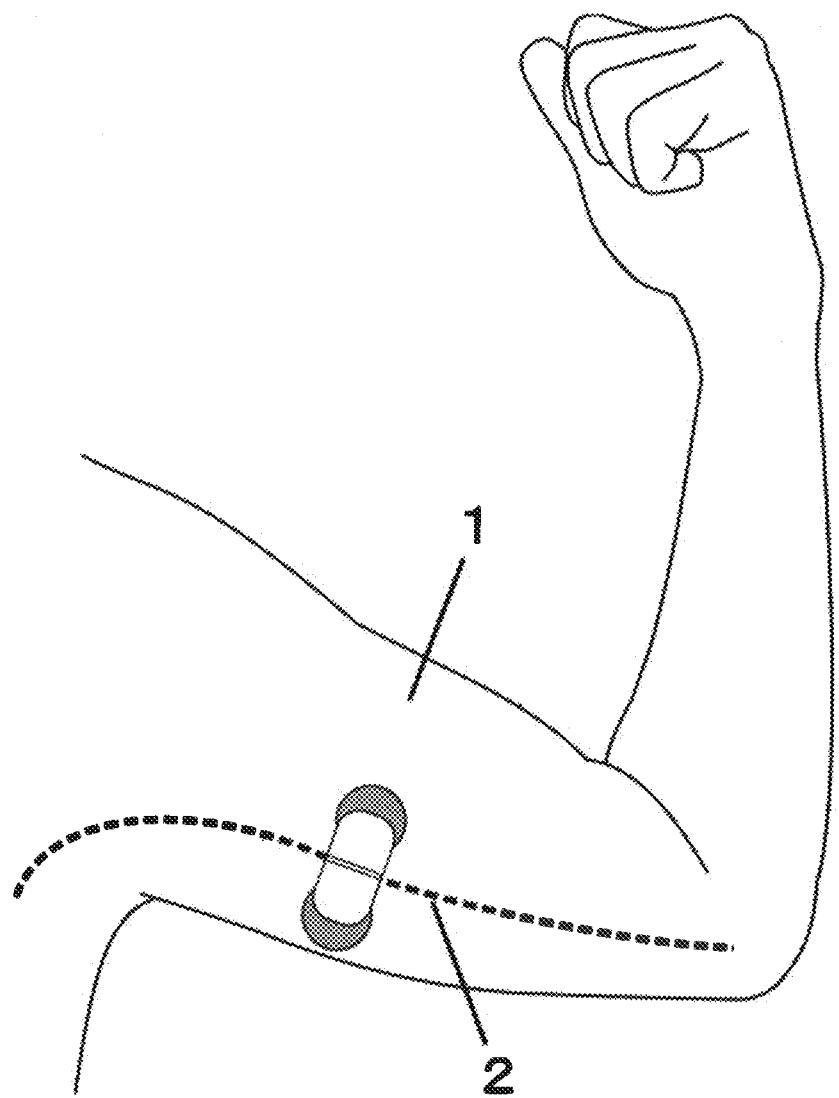
FIG. 5 is a schematic diagram illustrating the electrocardiogram measurement apparatus of the first example embodiment according to the present invention when being attached.

An electrocardiographic signal is obtained by the first electrode 101 and the second electrode 102 attached to the body surface (S207), and the result is output to the display unit 105 (S208). FIG. 5 illustrates a schematic diagram illustrating the electrocardiogram measurement apparatus 100 attached to an optimum position on the brachial artery 2 of the left upper arm 1. An electrocardiogram obtained in the first example embodiment is illustrated in the upper part of FIG. 6, and an I-lead electrocardiogram measured at the same time using an existing method is illustrated in the lower part of FIG. 6.

Note that when the electrocardiogram measurement apparatus 100 is used during an exercise, artifacts (noise introduced in an electrocardiogram) such as vibrations caused by the exercise and an electromyogram produced by muscles in the attachment location may occur and may disturb the waveform of an electrocardiogram. However, by adding a process of detecting such waveform disturbance and avoiding measurement during an exercise, erroneous detection can be avoided, and power consumption can be saved to extend service life. Further, by incorporating an acceleration sensor or the like that is capable of detecting an exercise state of a user, the presence of exercise can be identified more accurately.

Figure 7:
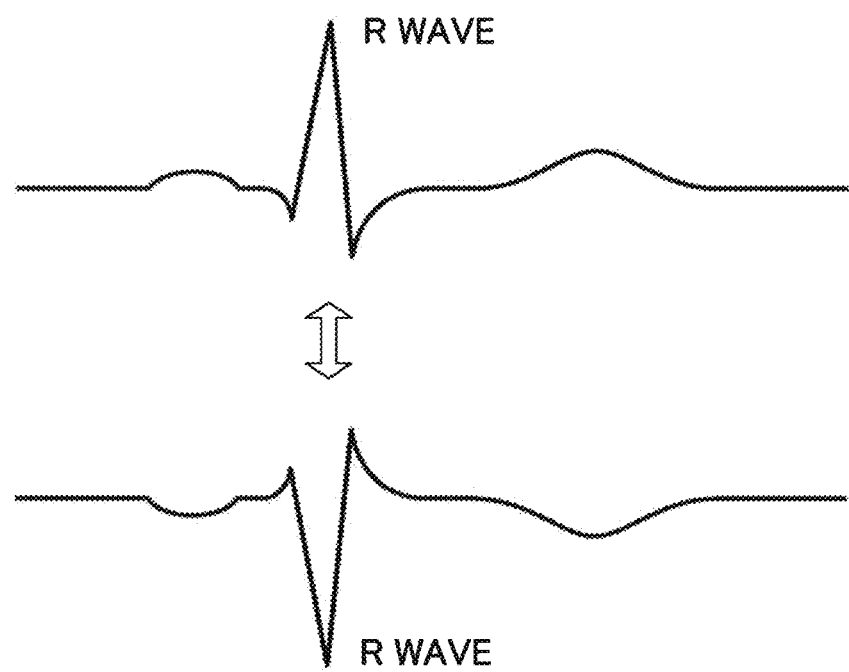
FIG. 7 is a conceptual diagram illustrating that the polarity of an electrocardiographic waveform is reversed by first and second electrodes crossing an artery.

When an electrocardiogram is measured, typically electrodes need to be attached to the chest, where the heart is located and a high signal intensity appears, or to be attached to either hands or feet, where a large potential difference appears. However, the inventors of the present invention have found that the signal polarity of electrocardiogram is reversed when the first and second electrodes cross an artery. FIG. 7 is a conceptual diagram illustrating polarity reversal of an electrocardiographic waveform caused by the first and second electrodes crossing an artery. By using this phenomenon, the potential difference between electrodes attached across an artery can be calculated and an electrocardiogram can be measured even with a very faint signal. Since signal-to-noise ratio (S/N ratio) is largest in a location where the potential difference between the first and second electrodes is largest at a region in which potential reversal is observable, it is desirable to perform measurement at the location.

Figure 6:
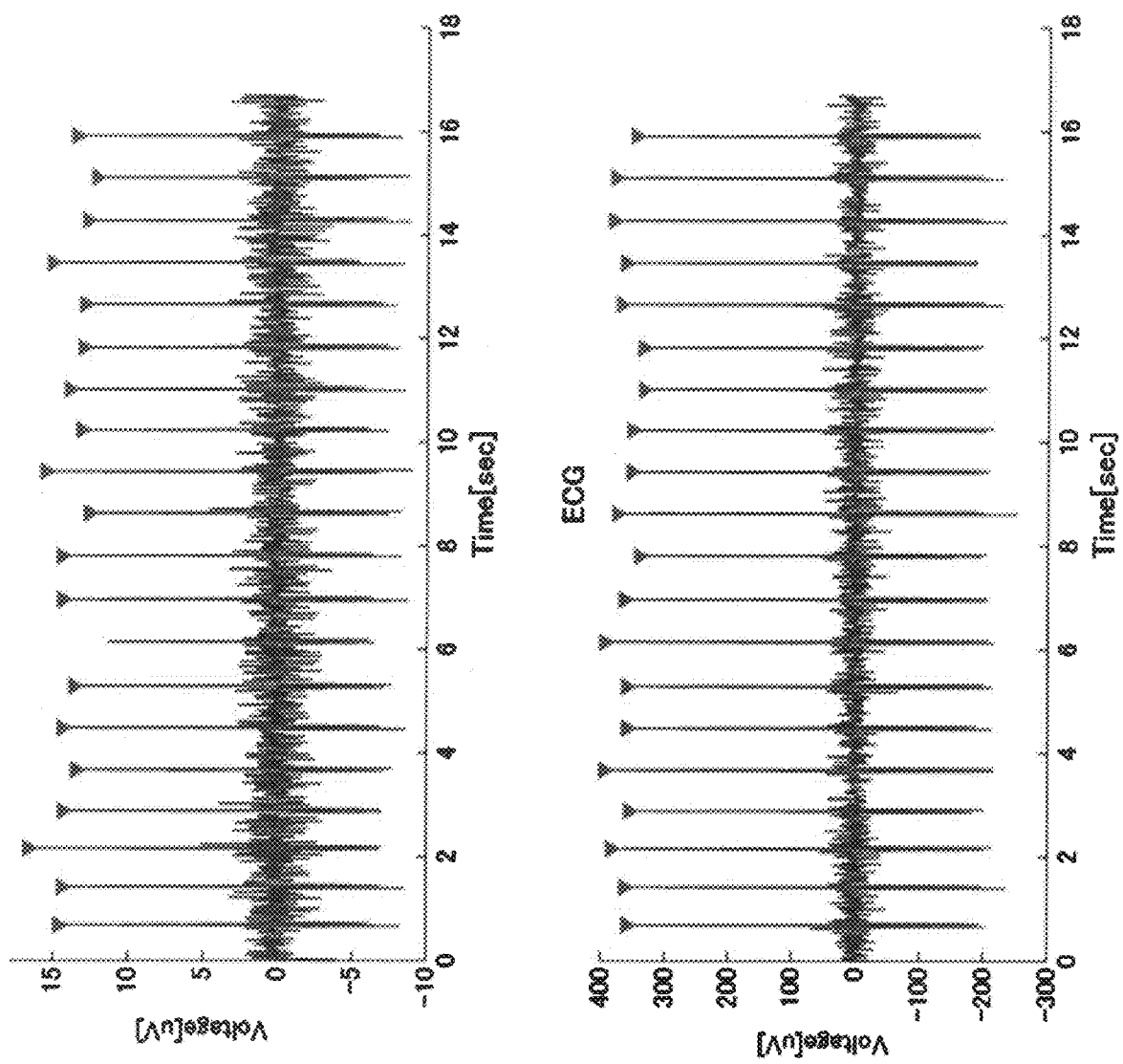
FIG. 6 illustrates a result of electrocardiogram measurement using a method of the first example embodiment according to the present invention and a result of electrocardiogram measurement using a related-art method.

Comparison between the R wave on the vertical axis of the electrocardiogram measured by the method of the present example embodiment and the R wave in the electrocardiogram measured by the existing method in FIG. 6 illustrates that the potential difference in the present example embodiment is about ½₀ of that in the existing method and thus a very faint electrocardiogram can be measured in the present example embodiment. The down-pointing triangles in the figure indicate R-wave peaks.

Further, an artery position can be found from a body surface in the present example embodiment and electrodes may be simply attached to an optimum position by aligning the electrodes with the artery position. Therefore, only two electrodes are required, rather than many electrodes as in PTL 1. Accordingly, the signal processing time can be reduced. Further, since electrodes do not need to be attached to many regions such as the chest, hands and feet but only to one region (the upper arm in the present example embodiment), attaching stress on the user is small. In addition, since only two electrodes are to be attached, even a user without expertise can easily measure an electrocardiogram.

Note that an electrocardiogram is measured in a position where the largest potential difference between the first and second electrodes appears in the present example embodiment. However, polarity reversal occurs also in an area surrounding the position where the largest potential difference appears and therefore an electrocardiogram may be measured in the such area. Although the potential difference in the area surrounding the position is about one half of the largest potential difference in the position and the S/N ratio is lower, the measurement is possible.

Further, if the position of an artery is known from experience of measuring with the electrocardiogram measurement apparatus 100 several times, the artery position indication mark 107 may be aligned with the position to attach the electrocardiogram measurement apparatus 100 without using the artery position measurement unit 104.

A speaker may be provided instead of the display unit 105 and the user may be notified by sound or voice when the electrocardiogram measurement apparatus 100 reaches or approaches an optimum position.

The artery position indication mark 107 may be a groove instead of a raised portion. Alternatively, the artery position indication mark 107 may be a portion colored in a color different from the color of the other parts of the housing instead of a raised portion or a groove. A raised portion or a groove may be formed and colored.

Second Example Embodiment

Figure 8:
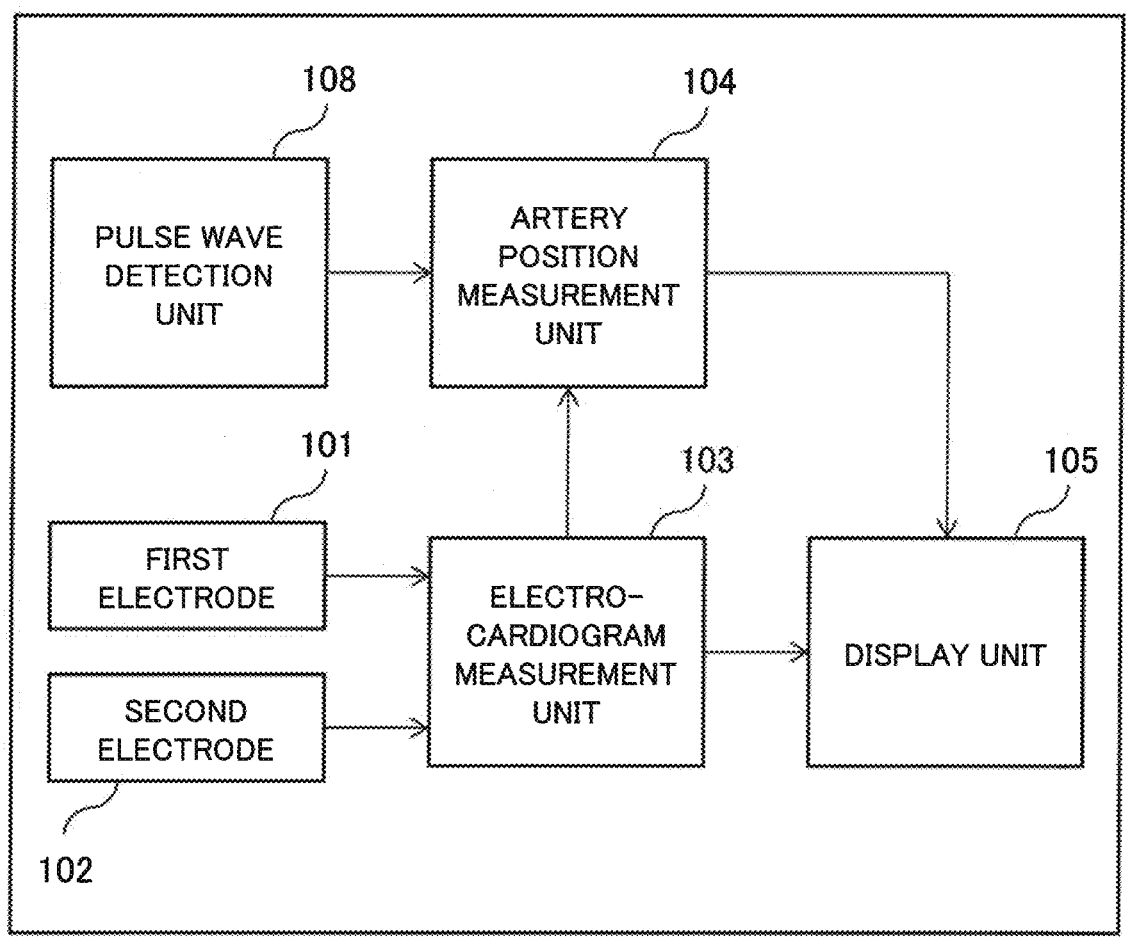
FIG. 8 is a block diagram of an electrocardiogram measurement apparatus of a second example embodiment according to the present invention.
Figure 9:
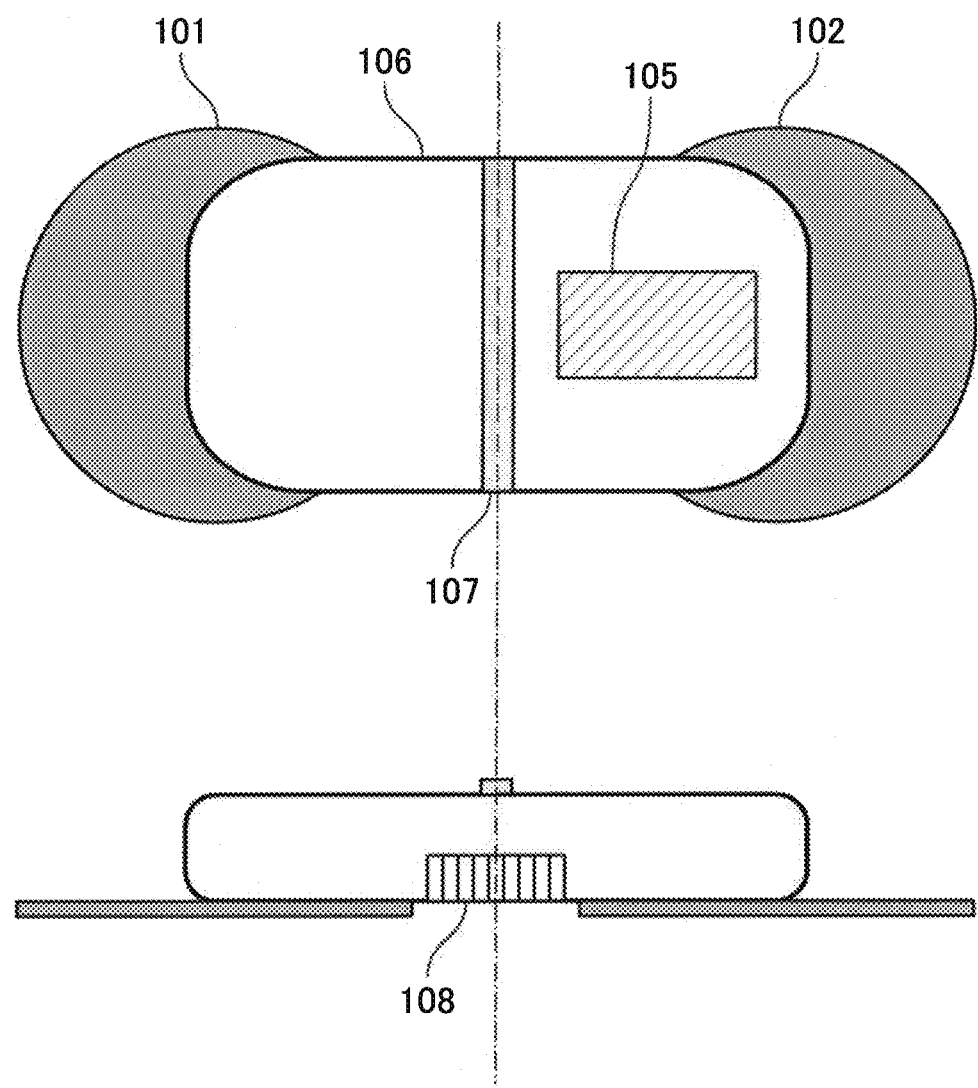
FIG. 9 illustrates a plan view and a cross-sectional view of the electrocardiogram measurement apparatus of the second example embodiment according to the present invention.

FIG. 8 illustrates a block diagram of an electrocardiogram measurement apparatus in a second example embodiment according to the present invention. The electrocardiogram measurement apparatus 100 includes a first electrode 101, a second electrode 102, a pulse wave detection unit 108, an electrocardiogram measurement unit 103, an artery position measurement unit 104, and a display unit 105. FIG. 9 illustrates a plan view and a cross-sectional view of the electrocardiogram measurement apparatus 100. The pulse wave detection unit 108 is disposed at the center between the first electrode 101 and the second electrode 102 on a side facing a body surface, and is any one of a vibration sensor, an optical sensor, an ultrasonic sensor, an electromagnetic wave sensor, a capacitance sensor, an electric field sensor, or a magnetic field sensor. Alternatively, a plurality of sensors of one or more of these types may be used.

Figure 10:
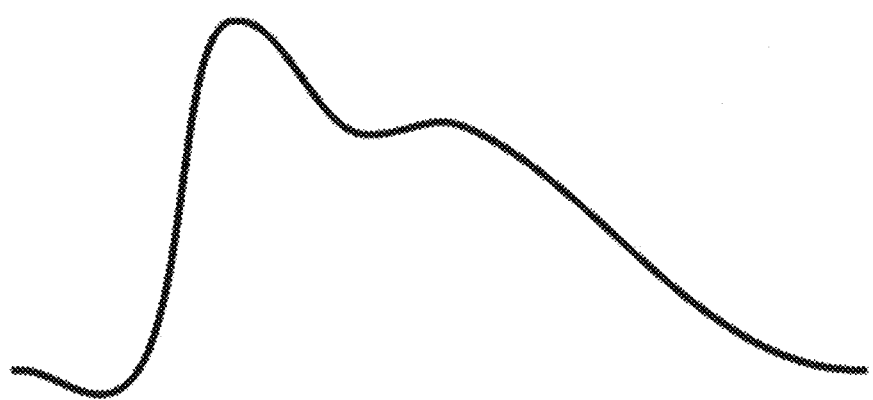
FIG. 10 illustrates a basic waveform of a pulse wave.

Differences from the first example embodiment are addition of the pulse wave detection unit 108 and a function of the artery position measurement unit 104. The pulse wave detection unit 108 captures pulsation of an artery under a body surface in contact with the pulse wave detection unit 108 and sends a signal of a pulse wave such as vibration caused by the pulsation to the artery position measurement unit 104. FIG. 10 illustrates a basic waveform of a pulse wave. The artery position measurement unit 104 estimates a position of the artery from the pulse wave and an electrocardiogram. Since the position in which the pulse wave signal is largest coincides with an area in which signal polarity of an electrocardiographic waveform is reversed, the area is identified as the position of the artery and an electrocardiogram is measured there. In the present example embodiment, as in the first example embodiment, the measurement is performed in the position in which the potential difference between the first and second electrodes is largest.

As described in the first example embodiment, the electrocardiogram measurement apparatus 100 can measure an electrocardiogram when there is an artery between the first electrode 101 and the second electrode 102. Accordingly, in a location farther away from an artery, one may be unable to determine in which direction the electrodes should be moved. However, when a pulse wave is measured as well, an optimum position can be easily found simply by moving the first and second electrodes in a direction in which a measured value of the pulse wave increases to find a direction in which the potential difference increases.

Figure 11:
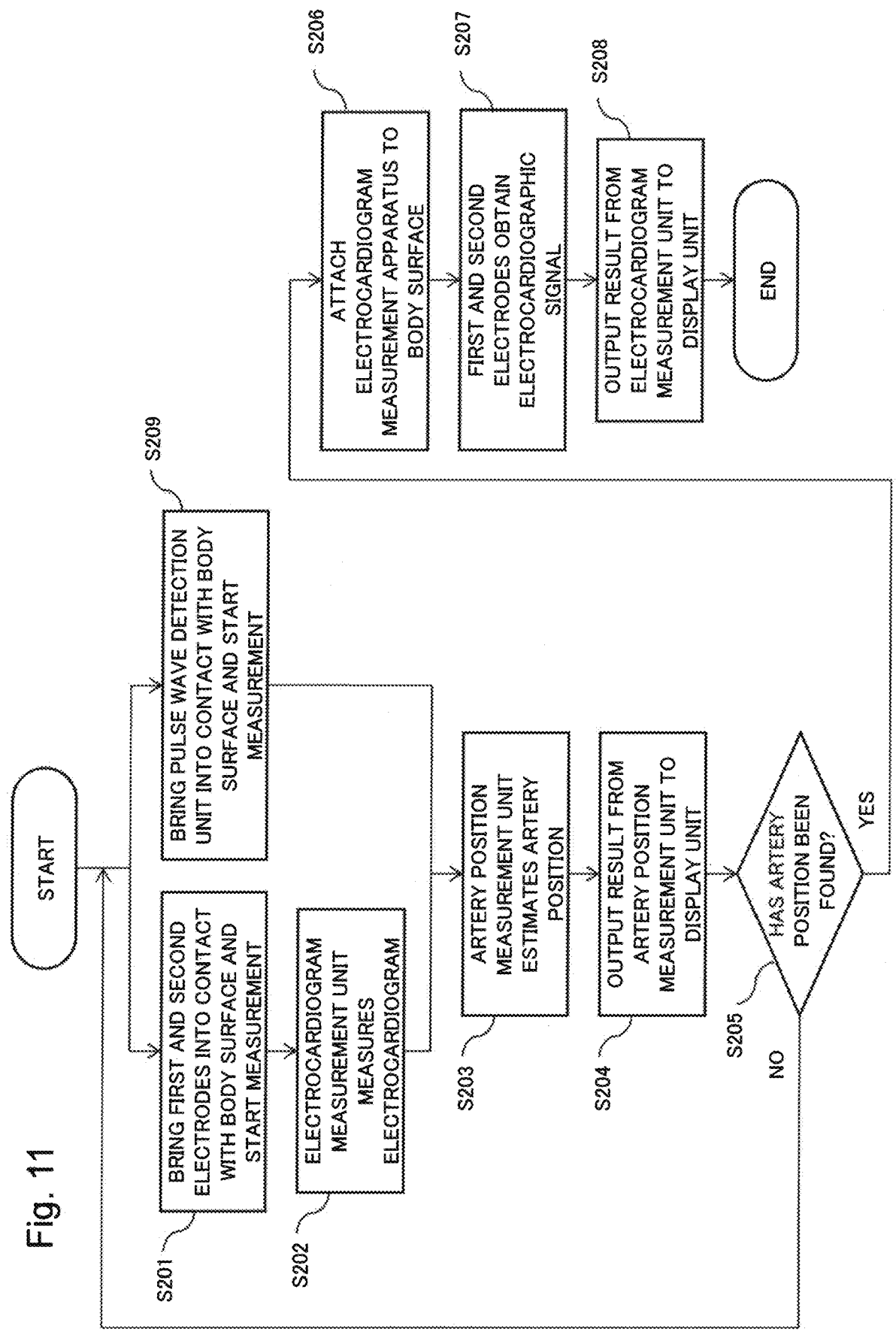
FIG. 11 is a flowchart of an operation procedure in the second example embodiment according to the present invention.

FIG. 11 illustrates a flowchart of the second example embodiment. The flowchart differs from the flowchart of the first example embodiment in FIG. 4 in that a pulse wave measurement process S209 is performed in parallel with the process of measuring an electrocardiogram with the first electrode 101 and the second electrode 102 in contact with a body surface near an artery (S201→S202). A user brings the electrocardiogram measurement apparatus 100 into contact with a body surface near an artery in order to detect a position of the artery. In the second example embodiment, the electrodes can be attached to a more accurate position because the position of the artery is estimated using not only an electrocardiogram but also a pulse wave which can be obtained from the artery (S209).

Third Example Embodiment

Figure 12:
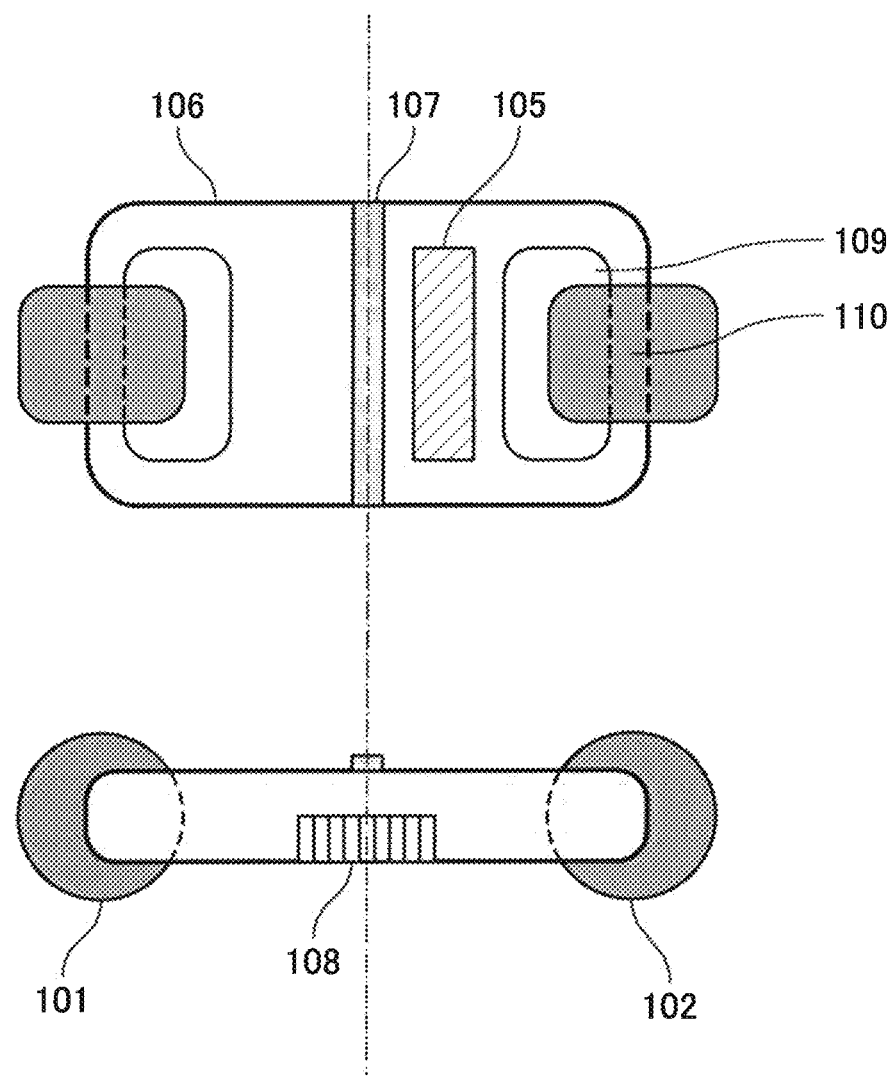
FIG. 12 illustrates a plan view and a cross-sectional view of an electrocardiogram measurement apparatus of a third example embodiment according to the present invention.

FIG. 12 illustrates a plan view and a cross-sectional view of an electrocardiogram measurement apparatus in a third example embodiment. The third example embodiment differs from the second example embodiment in that a cylindrical rotation shaft 110 is provided at both ends of a housing 106 and through holes 109 are formed in locations in the housing on the inner side from the rotation shafts 110. A first electrode 101 and a second electrode 102 are cylindrical, a hollow portion of each cylinder is fitted over each of the rotation shafts 110, and the first electrode 101 and the second electrode 102 rotate about the respective rotation shafts 110. Portions of the rotation shafts 110 that contact the first electrode 101 and the second electrode 102 are conductors such that electrical connections can be provided even while the first and second electrodes are rotating. The rotation shafts 110 are electrically connected to an electrocardiogram measurement unit 107.

A user brings the electrocardiogram measurement apparatus 100 into contact with a body surface near an artery in order to locate the artery. As in the second example embodiment, the user changes and adjusts the position of the electrocardiogram measurement apparatus 100 while observing information indicating the position of the artery displayed on a display unit 105.

Figure 13:
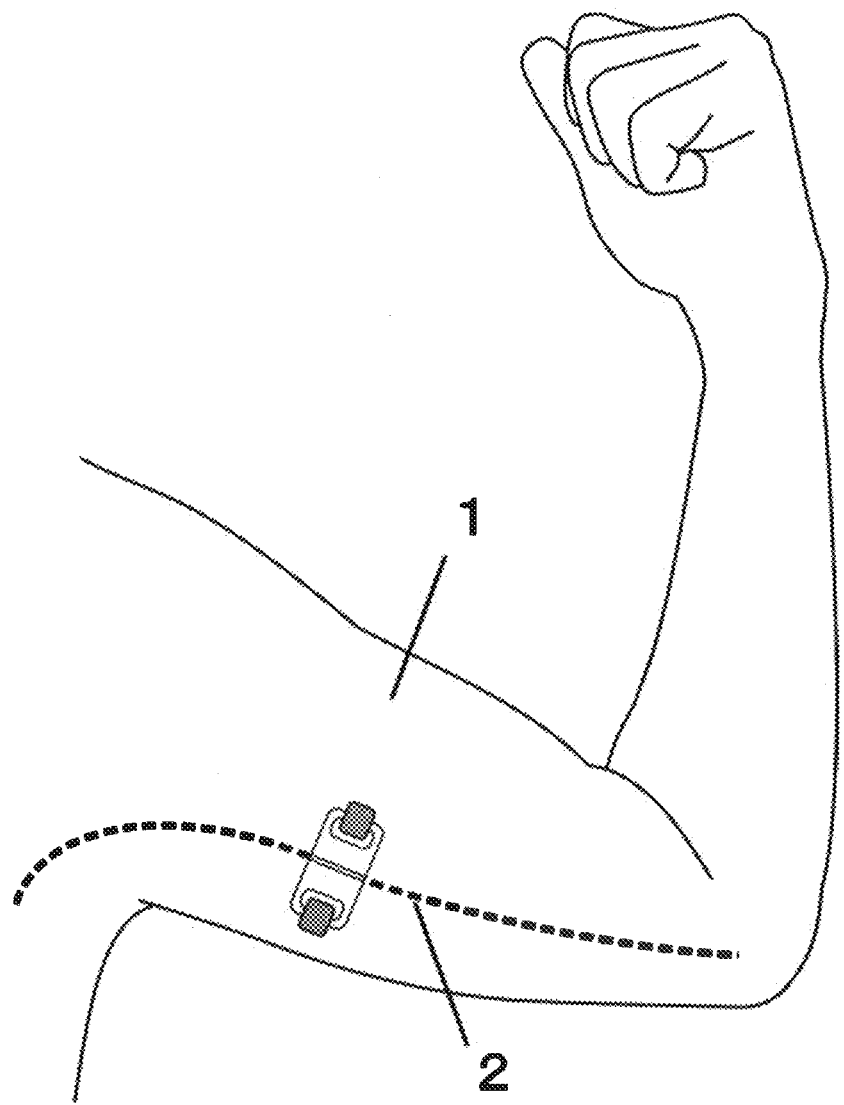
FIG. 13 is a schematic diagram of the electrocardiogram measurement apparatus of the third example embodiment according to the present invention when being attached.

In the third example embodiment, the first electrode 101 and the second electrode 102 can be moved by rolling over a body surface since the first electrode 101 and the second electrode 102 are cylindrical. FIG. 13 illustrates the electrocardiogram measurement apparatus positioned and attached.

Adhesion of the first electrode 101 and the second electrode 102 in the present example embodiment can possibly be insufficient since the areas of the first electrode 101 and the second electrode 102 that contact a body surface are small. If this is the case, the entire electrocardiogram measurement apparatus 100 may be fixed by wrapping an elastic band or the like after the position of the artery is determined.

Fourth Example Embodiment

Figure 14:
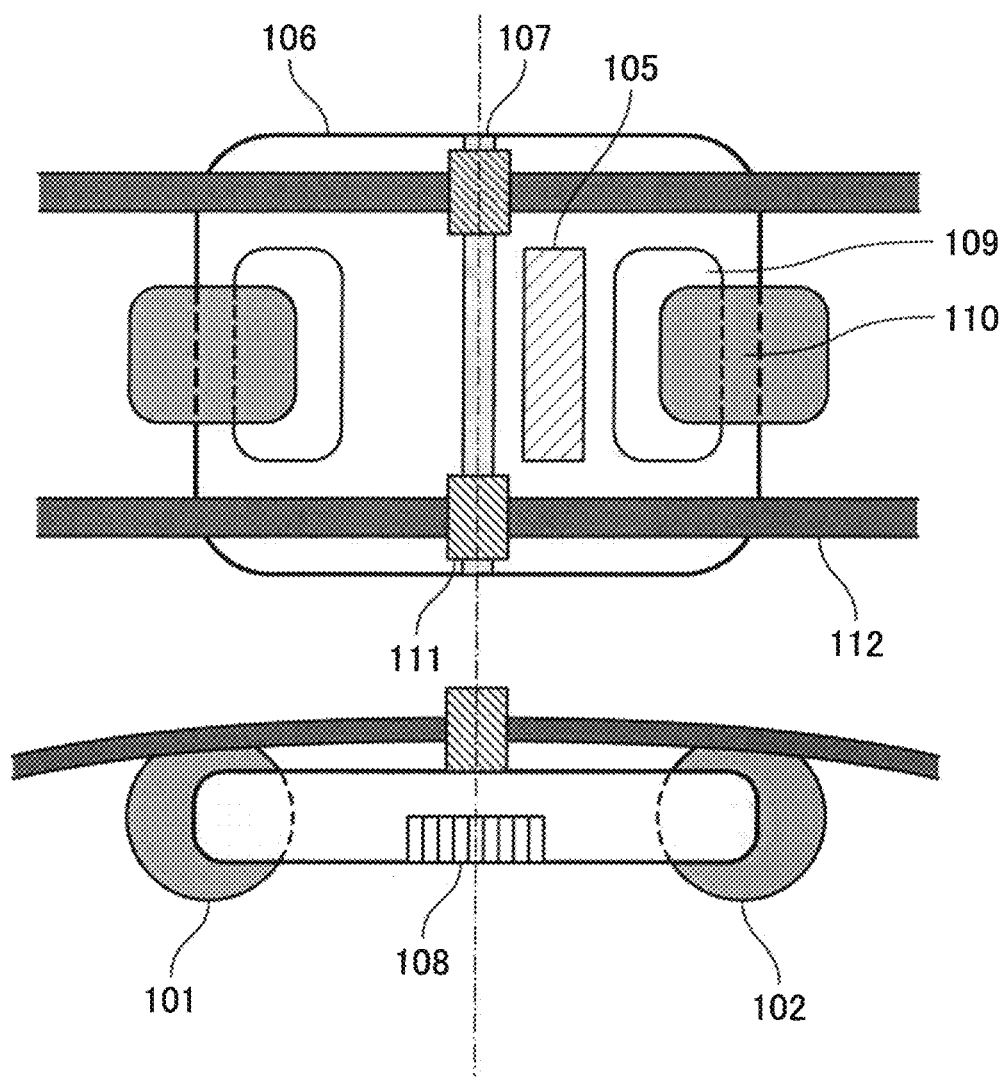
FIG. 14 illustrates a plan view and a cross-sectional view of an electrocardiogram measurement apparatus of a fourth example embodiment according to the present invention.
Figure 15:
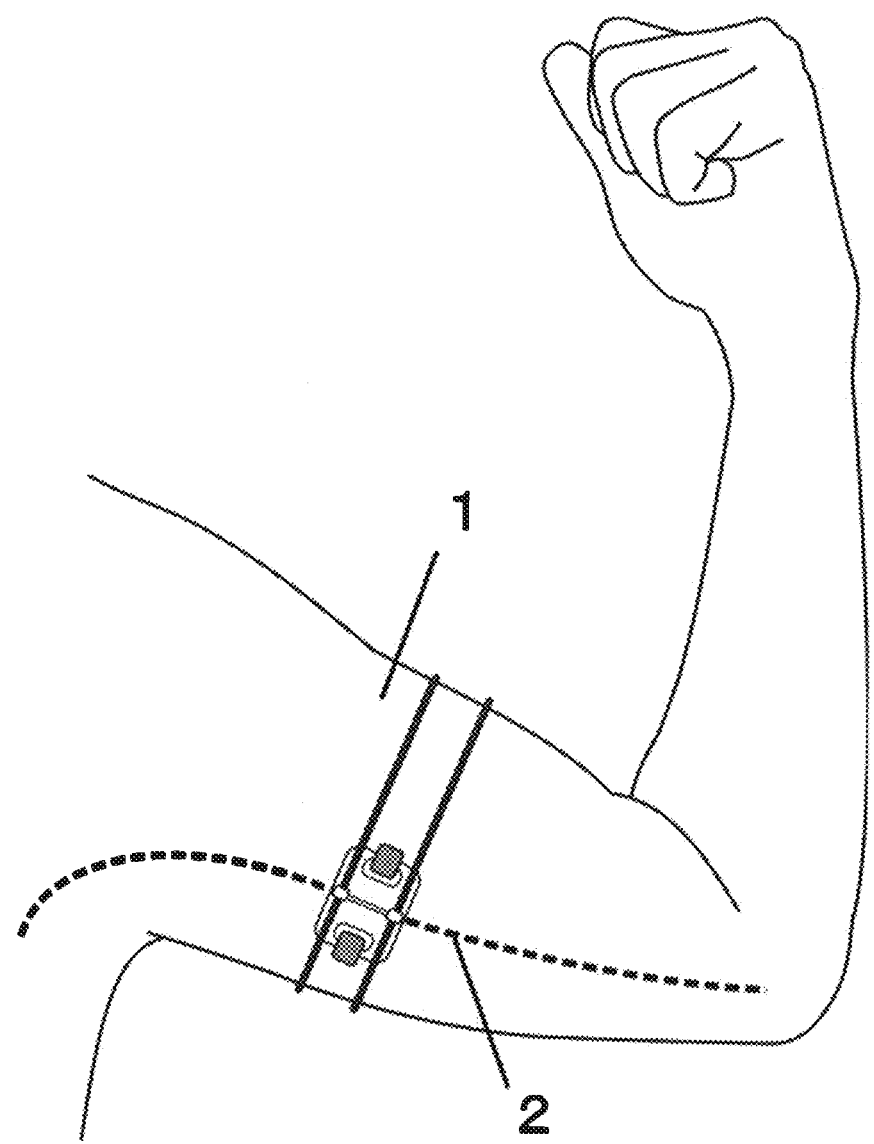
FIG. 15 is a schematic diagram of the electrocardiogram measurement apparatus of the fourth example embodiment according to the present invention when being attached.

FIG. 14 illustrates a plan view and a cross-sectional view of an electrocardiogram measurement apparatus in a fourth example embodiment. The fourth example embodiment differs from the third example embodiment in that a repositioning unit is included. The repositioning unit includes rings 111 and rails 112, the rings 111 are fixed to a housing 106, fitted into the rails 112, and move on the rails 112. This allows a first electrode 101, a second electrode 102, and a pulse wave detection unit 108 to move in parallel in the arm circumferential direction. In this way, the first electrode 101, the second electrode 102 and the pulse wave detection unit 108 can be moved so as to ensure that the first electrode 101, the second electrode 102 and the pulse wave detection unit 108 pass over the artery. FIG. 15 illustrates how the electrocardiogram measurement apparatus 100 is attached.

The repositioning unit in FIGS. 14 and 15 moves the first electrode 101, the second electrode 102 and the pulse wave detection unit 108 without changing their relative positions. Once an optimum position is determined, the first electrode 101 and the second electrode 102 are fixed at the position with the adhesion of the first electrode 101 and the second electrode 102 and an electrocardiogram is measured. Adhesion may be also provided to the side of the housing 106 that faces a body surface.

Note that the housing 106 may be separated into three, namely a first electrode portion, a second electrode portion and the other portion, in the direction in which the rails 112 extend, rings 111 to be coupled to the rails 112 may be provided in each of the portions in such a way that the three separate portions can individually move in the direction in which the rails 112 extend.

Once an artery position is determined, the repositioning unit may be removed from the electrocardiogram measurement apparatus 100 and then an electrocardiogram may be measured.

Other Example Embodiments

While electrocardiographic waveforms are measured over a brachial artery in the first to fourth example embodiments, an electrocardiogram may be measured over at least a carotid artery, superficial temporal artery, facial artery, radial artery, femoral artery, popliteal artery, posterior tibial artery and dorsal pedis artery, instead of a brachial artery.

While it is assumed in the first to fourth example embodiments that the user is a person on whom an electrocardiogram is measured, the user is not limited thereto and may be a doctor, a nurse, a caretaker, a family member, or the like.

While a display 105 or a speaker is used as an example of the notification unit in the first to fourth example embodiments, the notification unit 105 may be a wireless transmission unit that wirelessly transmits measurement data to a receiver outside the housing.

The whole or part of the example embodiments disclosed above can be described as, but not limited to, the following supplementary notes.

Supplementary Note 1

An electrocardiogram measurement apparatus including: a first electrode and a second electrode designed to be brought into contact with a body surface near an artery; an electrocardiogram measurement means for measuring a signal obtained from the first electrode and the second electrode; an artery position measurement means for identifying an area in which polarity of a measured signal is reversed as a position of an artery; and a notification means for notifying a user of information indicating the position of an artery.

Supplementary Note 2

An electrocardiogram measurement apparatus including: a first electrode and a second electrode designed to be brought into contact with a body surface near an artery; an electrocardiogram measurement means for measuring a signal obtained from the first electrode and the second electrode; an artery position measurement means for identifying a position in which a measured value of the measured signal is largest as a position of an artery; and a notification means for providing information indicating the position of the artery to a user.

Supplementary Note 3

The electrocardiogram measurement apparatus according to supplementary note 1 or 2, further including a pulse wave detection means for detecting a pulse wave signal and outputting the pulse wave signal to the artery position measurement means.

Supplementary Note 4

The electrocardiogram measurement apparatus according to supplementary note 3, wherein the first electrode, the second electrode and the pulse wave detection means are moved in a direction in which the measured value of the signal increases depending on a measured value from the artery position measurement means.

Supplementary Note 5

The electrocardiogram measurement apparatus according to any one of supplementary notes 1 to 4, wherein surfaces of the first electrode and the second electrode are adhesive.

Supplementary Note 6

The electrocardiogram measurement apparatus according to any one of supplementary notes 1 to 5, including repositioning means for allowing the first electrode and the second electrode to be moved depending on a measured value from the artery position measurement means.

Supplementary Note 7

The electrocardiogram measurement apparatus according to any one of supplementary notes 3 to 6, wherein the pulse wave detection means uses at least one of a vibration sensor, an optical sensor, an ultrasonic sensor, an electromagnetic wave sensor, a capacitance sensor, an electric field sensor, or a magnetic field sensor.

Supplementary Note 8

The electrocardiogram measurement apparatus according to any one of supplementary notes 1 to 7, wherein the first electrode and the second electrode are cylindrical and rotatable.

Supplementary Note 9

The electrocardiogram measurement apparatus according to any one of supplementary notes 1 to 8, wherein an indication mark is provided on an housing, the indication mark being a marker for positioning the electrocardiogram measurement apparatus over the position of an artery.

Supplementary Note 10

The electrocardiogram measurement apparatus according to any one of supplementary notes 1 to 9, wherein the artery is at least one of a brachial artery, a carotid artery, a superficial temporal artery, a facial artery, a radial artery, a femoral artery, a popliteal artery, a posterior tibial artery and a dorsal pedis artery.

Supplementary Note 11

The electrocardiogram measurement apparatus according to any one of supplementary notes 3 to 10, wherein the pulse wave detection means is positioned in a center between the first electrode and the second electrode.

Supplementary Note 12

The electrocardiogram measurement apparatus according to any one of supplementary notes 7 to 10, wherein a rotation shaft is provided at both end means of an housing containing the electrocardiogram measurement apparatus, through holes are provided in locations in the housing on the inner side from the rotation shafts, and the cylindrical first and second electrodes are fitted in the rotation shafts.

Supplementary Note 13

The electrocardiogram measurement apparatus according to any one of supplementary notes 6 to 11, wherein the repositioning means are rings fixed to the housing and rails passing through the rings.

Supplementary Note 14

An electrocardiogram measurement method including: measuring a signal obtained from a first and a second electrode while moving the first electrode and the second electrode in contact with a body surface; and measuring an electrocardiogram using an area in which polarity of the measured signal is reversed as a position of an artery.

Supplementary Note 15

The electrocardiogram measurement method according to supplementary note 1, wherein a position in which a measured value of the signal is largest in the area in which polarity of the signal is reversed is identified as a position of an artery.

The present invention has been described using the example embodiments described above as model examples. However, the present invention is not limited to the example embodiments described above. Specifically, the present invention can employ various modes that can be understood by those skilled in the art within the scope of the present invention.

This application is based upon and claims the benefit of priority from Japanese Patent Application No. 2015-207322 filed on Oct. 21, 2015, the entire disclosure of which is incorporated herein.

REFERENCE SIGNS LIST

1 Left upper arm
2 Brachial artery
100 Electrocardiogram measurement apparatus
101 First electrode
102 Second electrode
103 Electrocardiogram measurement unit
104 Artery position measurement unit
105 Display unit
106 Housing
107 Artery position indication mark
108 Pulse wave detection unit
109 Through hole
110 Rotation shaft
111 Ring
112 Rail

What is claimed is:
1. An electrocardiogram measurement apparatus comprising:
   a first electrode and a second electrode to be brought into contact with a body surface near an artery;
   an electrocardiogram measurement unit that measures a signal obtained from the first electrode and the second electrode;
   an artery position measurement unit that identifies an area in which polarity of the measured signal is reversed as a position of the artery; and a notification unit that notifies a user of information indicating the position of the artery.

2. The electrocardiogram measurement apparatus according to claim 1, further comprising: a pulse wave detection unit that detects a pulse wave signal and outputs the pulse wave signal to the artery position measurement unit.

3. The electrocardiogram measurement apparatus according to claim 2, wherein the first electrode, the second electrode and the pulse wave detection unit are moved in a direction in which a measured value of the signal increases depending on a measured value from the artery position measurement unit.

4. The electrocardiogram measurement apparatus according to claim 2, wherein the pulse wave detection unit is positioned in a center between the first electrode and the second electrode.

5. The electrocardiogram measurement apparatus according to claim 1, wherein surfaces of the first electrode and the second electrode are adhesive.

6. The electrocardiogram measurement apparatus according to claim 1, further comprising a repositioning unit that enables the first electrode and the second electrode to be moved depending on a measured value from the artery position measurement unit.

7. The electrocardiogram measurement apparatus according to claim 6, wherein the repositioning unit is rings fixed to the housing and rails passing through the rings.

8. The electrocardiogram measurement method according to claim 7, wherein a position in which a measured value of the signal is largest in the area in which polarity of the signal is reversed is identified as a position of an artery.

9. The electrocardiogram measurement apparatus according to claim 2, wherein the pulse wave detection unit uses at least one of a vibration sensor, an optical sensor, an ultrasonic sensor, an electromagnetic wave sensor, a capacitance sensor, an electric field sensor, and a magnetic field sensor.

10. The electrocardiogram measurement apparatus according to claim 9, wherein a rotation shaft is provided at both end of a housing containing the electrocardiogram measurement apparatus, through holes are provided in locations in the housing on the inner side from the rotation shafts, and the cylindrical first and second electrodes are fitted in the rotation shafts.

11. The electrocardiogram measurement apparatus according to claim 1, wherein the first electrode and the second electrode are cylindrical and rotatable.

12. The electrocardiogram measurement apparatus according to claim 1, wherein an indication mark is provided on a housing, the indication mark being a marker for positioning the electrocardiogram measurement apparatus over the position of an artery.

13. The electrocardiogram measurement apparatus according to claim 1, wherein the artery is at least one of a brachial artery, a carotid artery, a superficial temporal artery, a facial artery, a radial artery, a femoral artery, a popliteal artery, a posterior tibial artery and a dorsal pedis artery.

14. An electrocardiogram measurement apparatus comprising:
a first electrode and a second electrode to be brought into contact with a body surface near an artery;
an electrocardiogram measurement unit that measures a signal obtained from the first electrode and the second electrode;
an artery position measurement unit that identifies a position at which a measured value of the measured signal is largest as a position of the artery; and
a notification unit that notifies a user of information indicating the position of the artery.

15. An electrocardiogram measurement method comprising:
measuring an electrocardiogram signal obtained from a first electrode and a second electrode while moving the first electrode and the second electrode in contact with a body surface; and
acquiring an area where polarity of the electrocardiogram signal is reversed is the position of the artery.

* * * * *